(12) United States Patent
Adaniya et al.

(10) Patent No.: US 6,960,185 B2
(45) Date of Patent: Nov. 1, 2005

(54) SUBCUTANEOUS ACCESS PORT

(75) Inventors: George Adaniya, Wellesley, MA (US); Paul V. Fenton, Jr., Marblehead, MA (US)

(73) Assignee: Alphaport, LLC, Wellesley, MA (US)

( * ) Notice: Subject to any disclaimer, the term of this patent is extended or adjusted under 35 U.S.C. 154(b) by 351 days.

(21) Appl. No.: 09/834,350

(22) Filed: Apr. 13, 2001

(65) Prior Publication Data

US 2001/0037094 A1 Nov. 1, 2001

Related U.S. Application Data

(60) Provisional application No. 60/197,191, filed on Apr. 14, 2000.

(51) Int. Cl.$^7$ .............................................. A61M 31/00
(52) U.S. Cl. .................................................. 604/93.01
(58) Field of Search .......................... 604/890.1–891.1, 604/93.01, 115–117, 246–247, 256, 288.01–288.04

(56) References Cited

U.S. PATENT DOCUMENTS

| | | | |
|---|---|---|---|
| 4,915,690 A | | 4/1990 | Cone et al. |
| 5,013,298 A | * | 5/1991 | Moden et al. ......... 604/288.02 |
| 5,057,084 A | | 10/1991 | Ensminger et al. |
| 5,178,642 A | * | 1/1993 | Fenton, Jr. .................. 604/533 |
| 5,180,365 A | | 1/1993 | Ensminger et al. ........... 604/93 |
| 5,281,199 A | | 1/1994 | Ensminger et al. ........... 604/93 |
| 5,702,363 A | | 12/1997 | Flaherty ...................... 604/93 |
| 5,741,228 A | | 4/1998 | Lambrecht et al. ........... 604/93 |
| 5,840,063 A | | 11/1998 | Flaherty ...................... 604/93 |
| 5,848,989 A | * | 12/1998 | Villani ................... 604/288.02 |

FOREIGN PATENT DOCUMENTS

| | | |
|---|---|---|
| WO | WO 97/12643 | 4/1997 |
| WO | WO 97/37718 | 10/1997 |
| WO | WO 97/47338 | 12/1997 |
| WO | WO 98/31272 | 7/1998 |
| WO | WO 98/31416 | 7/1998 |
| WO | WO 98/51368 | 11/1998 |
| WO | WO 99/03519 | 1/1999 |

* cited by examiner

*Primary Examiner*—LoAn H. Thanh
(74) *Attorney, Agent, or Firm*—McDermott Will & Emery LLC

(57) ABSTRACT

An implantable access device including a port for receiving and guiding a filament, such as a needle, into an entry region of the device. The port includes a plate for receiving a filament, and at least two walls extending upwardly from the plate. The walls are shaped and positioned to guide the filament moving between opposing first and second ends of the plate through an entry region defined between the walls at the second end of the plate. Preferably, a greatest distance between the walls is at least five times greater than a height of the walls, so that the port provides a large filament strike area, yet has a small overall height. In addition, a greatest distance between the ends of the plate is also preferably at least five times greater than the height of the walls, to further increase the filament strike area without increasing height.

30 Claims, 4 Drawing Sheets

SUBCUTANEOUS ACCESS PORT

CROSS-REFERENCE TO RELATED APPLICATION

The present application claims priority from co-pending provisional U.S. Patent Application Ser. No. 60/197,191, filed Apr. 14, 2000, which is incorporated herein by reference in its entirety.

FIELD OF THE DISCLOSURE

The present disclosure generally relates to an apparatus for providing vascular access to a living body. More particularly, the disclosure relates to an improved needle-receiving port allowing repeated subcutaneous access to a region within the body of a patient.

BACKGROUND OF THE DISCLOSURE

During a course of medical treatment, it may be necessary to gain repeat access to specific sites, devices, tissues, or fluids within the body of a patient. This may be effected for the temporary or sustained infusion of various therapeutic agents, the removal and treatment of fluids, the injection of contrast agents, as well as the insertion of various treatment devices such as fiber-optic cameras and light sources, ultrasound probes, and thrombectomy catheters. A number of strategies are currently used to gain such access, including direct vessel cannulation, short and long term catheterization, as well as subcutaneous port and pump implantation.

Direct cannulation of a native or artificial vessel with a needle provides perhaps the least expensive and simplest form of access. However, repeat cannulation of superficial vessels has been shown to result in vessel thrombosis, and in case of hemodialysis graft cannulation, access stenosis and the formation of pseudoaneurisms. A patient's accessible vessels can quickly be eliminated by repeat direct cannulation during the course of some aggressive treatment regimens, limiting treatment options and worsening prognosis.

Short and long term catheters have been used to address the many problems of direct cannulation. These transcutaneous devices are generally flexible cannulae that are inserted percutaneously into the region of interest such as a blood vessel or the peritoneal cavity. Catheters have one or more lumens through which various fluids or devices can pass. While catheters allow repeat access with a reduced risk of vessel thrombosis, they suffer from a number of significant drawbacks. Aside from being unsightly and prone to inadvertent withdrawal, catheters often have complications with infection.

Subcutaneously implanted ports have increasingly been used as an alternative to transcutaneous catheterization. These devices provide a site beneath the skin that can be accessed by special non-coring needles through a percutaneous puncture at the time of treatment. The devices generally comprise a housing that forms a reservoir which communicates with a catheter that leads to the area requiring treatment. A self-sealing septum formed from a high density silicone elastomer spans the top of this reservoir, creating a continuous barrier against the passage of fluids such as blood that are in communication with the port. This septum is punctured by the needle to permit access to the reservoir. Once the needle is withdrawn, the septum closes, restoring the continuous barrier. Ports avoid repeated direct cannulation of a native vessel with a needle. By being completely implanted (that is, requiring no open passage through the skin), ports also avoid many of the infection complications of catheters. In addition, ports are generally better accepted by patients because the ports are less obtrusive, cannot be accidentally withdrawn, and are relatively easy to maintain.

Subcutaneously implanted ports are also used as a means of communicating with other implanted medical devices. For example, implantable infusion pumps that provide a sustained infusion of therapeutic agents into the body of a patient often use one or more integral ports as refilling and flushing sites.

Referring to FIG. 1, an existing implantable access port 10 is shown. The port 10, which is described in detail in U.S. Pat. No. 5,281,199, allows the introduction of various filaments including catheters and needles into the body of a patient without the use of a standard septum. By employing a variety of different valving mechanisms (not shown), the port 10 presumably has broader applications to more rigorous therapies requiring frequent access or high flow, i.e. therapies previously restricted to transcutaneous catheters and direct cannulation. The port 10 includes an access housing 12 which defines a funnel-shaped entrance orifice 14 having a decreasing cross-sectional open area which reduces down to focus area, or entrance opening 16, leading into an internal passageway (not shown) that connects to an exit opening 18. Access housing 12 can be supported subcutaneously by mounting platform 19 having holes 21 for use with sutures or staples.

One significant limitation of the port 10, however, is in the strike area, or the region that the medical professional attempting access must hit with the accessing filament to enter the funnel-shaped entrance orifice 14. A large strike area is critical for simple cannulation and for allowing each insertion wound to heal before that region must be re-cannulated. By nature, to increase the strike area of a generally funnel-shaped entrance orifice 14, one must also increase the funnel's overall size in three dimensions. A dimension of particular importance with ports is height, or depth below the skin. The taller, or deeper, a port, the more tension the port places on the insertion wound of a patient. Increasing the strike area of the funnel-shaped entrance orifice 14, therefore, necessarily increases the height of the port 10 and tension on the insertion wound of a patient.

The funnel-shaped entrance orifice 14 further limits the strike area by providing only a single focal point or entry point for the accessing filament. Because the filament is always focused to the same site, the same tissue proximal to that entry site must be traumatized during each access. Repeat trauma to tissue can lead to devascularization and necrosis, creating a potential site for infection.

Later implantable access ports 10' and 10", such as those shown in FIGS. 2 and 3, attempt to overcome the deficiencies of the port 10 of FIG. 1. These later ports 10' and 10", which are described in detail in U.S. Pat. No. 5,741,228, each include a housing 12' having an elongated open guidance channel 14' and 14", respectively, communicating with an entrance opening 16' of the housing. The entrance opening 16' leads into an internal passageway (not shown) of the housing 12', which is in turn in fluid communication with a housing exit opening 18'.

The guidance channels 14' and 14" both have a substantially constant cross sectional area. Furthermore, in the port 10' of FIG. 2, the guidance channel 14' has a generally V-shaped configuration, while in the port 10" of FIG. 3, the guidance channel 14" has a generally U-shaped configuration. The channels 14' and 14" are for receiving and guiding a filament toward and into the entrance opening 16'. The open guidance channels 14' and 14" allow for increases in accessing filament strike area without increasing the overall height of the ports 10'.

What is still desired, however, is an improved needle-receiving port for an implantable device allowing repeated subcutaneous access to a region within the body of a patient. Preferably, the port will provide an even greater filament strike area, yet have a relatively shorter height.

SUMMARY OF THE DISCLOSURE

The present disclosure, accordingly, is directed toward an implantable patient access device including a port for receiving and guiding a filament, such as a needle, into an entry region of the implantable device. The port includes a plate for receiving a filament, and at least two walls extending upwardly from the plate. The walls are shaped and positioned to guide the filament moving between opposing first and second ends of the plate through the entry region defined between the walls and located substantially at the second end of the plate.

A greatest distance between the walls is preferably at least five times greater than a height of the walls from the plate, so that the port provides a relatively large filament strike area, yet has a relatively short overall height. In addition, a greatest distance between the first and the second ends of the plate is also preferably at least five times greater than the height of the walls, to further increase the filament strike area. The large strike area of the presently disclosed port allows for multiple skin and tissue puncture sites along the port's length, yet the relatively short height of the port minimizes tension on the insertion wound of a patient.

These and other features and benefits of the present disclosure will become more apparent upon reading the following specification in conjunction with the accompanying drawing figures.

BRIEF DESCRIPTION OF THE DRAWINGS

Like reference characters designate identical or corresponding components and units throughout the several views.

DETAILED DESCRIPTION OF THE DISCLOSURE

Figure 4:
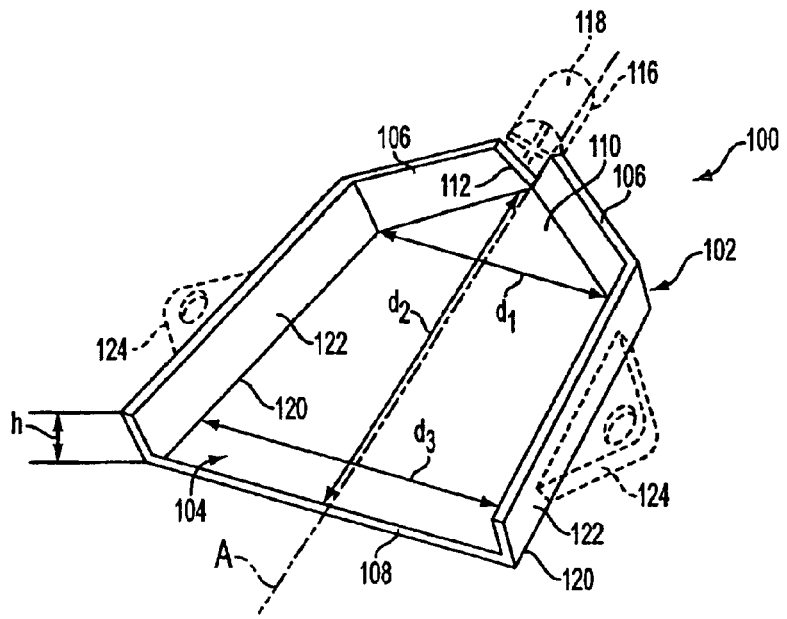
FIG. 4 is a perspective view of a needle-receiving port constructed in accordance with the present disclosure for use with an implantable patient access device.

Referring to FIG. 4, the present disclosure provides an implantable patient access device 100 including a port 102 for receiving and guiding a filament, such as a needle, into an entry region 112 of the implantable device. The port 102 includes a plate 104 for receiving a filament, and at least two walls 106 extending upwardly from the plate 104. In general, the walls 106 are shaped and positioned to guide a filament moving between opposing first and second ends 108, 110 of the plate 104 towards the entry region 112 defined between the walls 106 and located substantially at the second end 110 of the plate 104. In the particular embodiment shown, a distance between the walls 106 decreases monotonically towards the entry region 112, although a port constructed in accordance with the present disclosure is not limited to a monotonically decreasing distance between the walls.

In addition, a greatest distance "$d_1$" between the walls 106, which in the present embodiment corresponds to an overall width of the strike plate 104, is preferably at least five times greater than a greatest height "h" of the walls 106 from the plate 104, so that the port 102 provides a relatively large filament strike area, yet has a relatively short overall height. Moreover, a greatest distance "$d_2$" between the first and the second ends 108, 110 of the plate 104, e.g., the length of the plate, is also preferably at least five times greater than the height "h" of the walls 106, to additionally increase the filament strike area.

Figure 1:
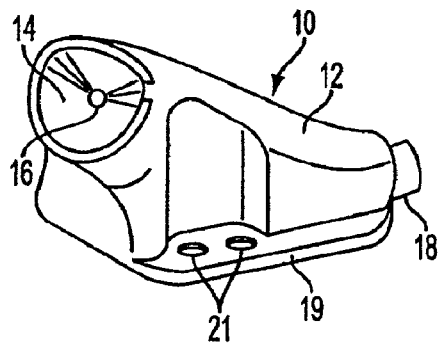
FIG. 1 is a perspective view of an implantable patient access device constructed in accordance with the prior art, and including a generally funnel-shaped needle guidance channel.
Figure 2:
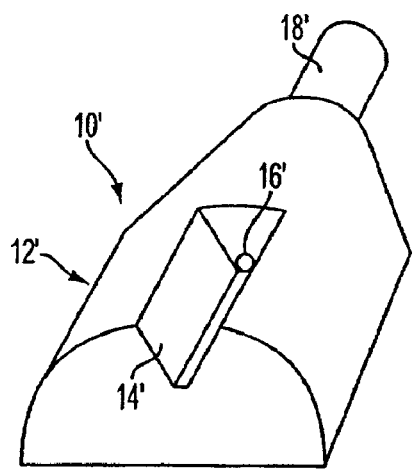
FIG. 2 is a perspective view of another implantable patient access device constructed in accordance with the prior art, and including a generally V-shaped needle guidance channel having substantially constant cross sectional area.
Figure 3:
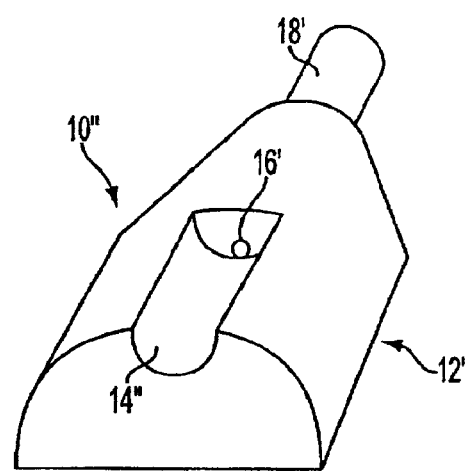
FIG. 3 is a perspective view of an additional implantable patient access device constructed in accordance with the prior art, and including a generally U-shaped needle guidance channel having substantially constant cross sectional area.
Figure 5:
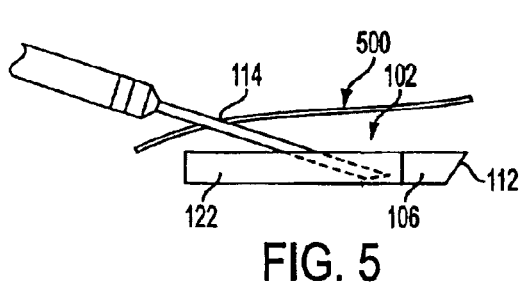
FIG. 5 is a side elevation view of the port of FIG. 4 shown receiving a needle.
Figure 6:
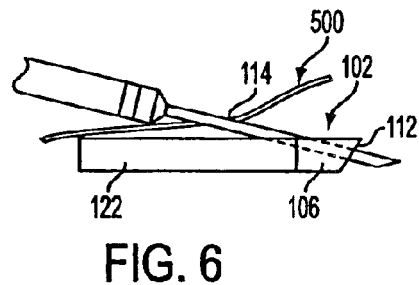
FIG. 6 is a side elevation view of the port of FIG. 4 shown guiding the needle.

Turning also to FIGS. 5 and 6, there is shown the port 102 of FIG. 4 implanted in a patient beneath an outer layer of skin, or epidermis 500, with an accessing filament 114 extending through the skin 500 and being received and guided within the port 102. Typically the filament would be a needle 114, as shown, but another substantially rigid member could also be used. In addition, the filament could comprise a more flexible element such as catheter. The port 102 of the present disclosure is meant as an integral functioning part of an implantable patient access device 100, such as a sustained infusion pump, or a catheter fluidly coupled to a vessel, a site, space, tissue, fluid, organ or another implanted device, or adaptable for independent implantation under the skin of a patient for communication with a site, space, tissue, fluid, vessel, organ, or the like. As shown in FIG. 1 with broken lines, in addition to the port 102, the implantable patient access device 100 can also include a valve assembly 116 positioned adjacent to the entry region 112 of the port 102. The valve assembly 116 is generally of the type that is normally closed and adapted to be opened by the filament 114 guided through the entry region 112 by the walls of the port 102. A simple exit tube 118 can extend from the valve assembly 116 for connection to a catheter fluidly coupled to a vessel, for example.

The port 102 disclosed herein has a number of advantages over the ports described in the prior art. First, the port 102 allows for an increase in strike area without an increase in overall port height. The large strike area allows for multiple skin and tissue puncture sites along the length of the port 102, yet the relatively short height of the port minimizes tension on the insertion wound of a patient. Of course, by puncturing different sites over the enlarged strike area during a treatment that requires repeat injections, for example, trauma to the same sites of skin and tissue can be minimized. The strike area of the port 102 can be chosen to fit the requirements of the specific therapy, allowing for an increase in overall strike area by increasing the size of the port 102 in only a single dimension or in two dimensions, without increasing the height of the port. The strike area is increased simply by increasing the length "$d_2$" or width "$d_1$" of the strike plate 104.

Referring again to FIG. 4, the second end 110 of the plate 104 is pointed and the entry region 112 between the walls corresponds with a tip of the second end furthest from the first end 108 of the plate 104. In addition, the port 102 includes a central axis "A" extending through the first and the second ends 108, 110 of the plate 104 and the point of the second end 110 of the plate 104 is aligned with the axis "A". The plate 104 also includes sides 120 extending between the ends 108, 110 of the plate 104.

Preferably, the at least two walls comprise end walls 106, and the port 102 further includes opposing side walls 122 extending from the sides 120 of the plate 104 and between the first end 108 of the plate and the end walls 106. The side walls 122 are shaped and positioned to guide the filament moving between the first end 108 and the second end 110 of the plate 104 towards the end walls 106, so that the end walls can guide the filament to the entry region 112. Preferably, a greatest distance "$d_3$" between the side walls 122 is equal to or greater than the greatest distance "$d_1$" between the end walls 106, although a port constructed in accordance with the present disclosure is not meant to be so limited. In the embodiment of FIG. 4, a distance between the side walls 122 decreases monotonically between the first and the second ends 108, 110 of the plate 104.

In the port 102 of FIGS. 4 through 6, the plate 104 is substantially flat, the side walls 122 are substantially planar and extend substantially perpendicularly from the sides 120 of the plate 104, and the end walls 106 are substantially planar and extend at an outward angle from the second end 110 of the plate 104. It should be understood however, that the side walls 122 can be provided to extend at an angle with respect to the plate 104, and the end walls 106 can be provided to extend perpendicularly from the second end 110 of the plate 104. In addition, the side walls 122, the end walls 106 and the plate 104 can be provided as curved or partially curved (for example, convex or concave, or some more complex curve) instead of flat, or otherwise shaped to encourage movement of the filament towards the entry region 112 of the port 102. Furthermore, the port can include other guiding elements, such a needle grooves formed in the plate 104 leading to the entry region 112.

The port 102, or at least top surfaces of the port 102, are made of a resilient material such as titanium, stainless steel or other metals, or a ceramic, that can endure frequent contact with the tip of an accessing filament such as a needle 114. The port 102 can also be provided with suture loop attachment wings 124 (shown in broken lines in FIG. 4) for facilitating fixation of the port 102 within the body. Alternatively, the exterior surface of the port 102 can be roughened or porous, promoting tissue ingrowth to help fix the port 102 within the patient.

Figure 7:
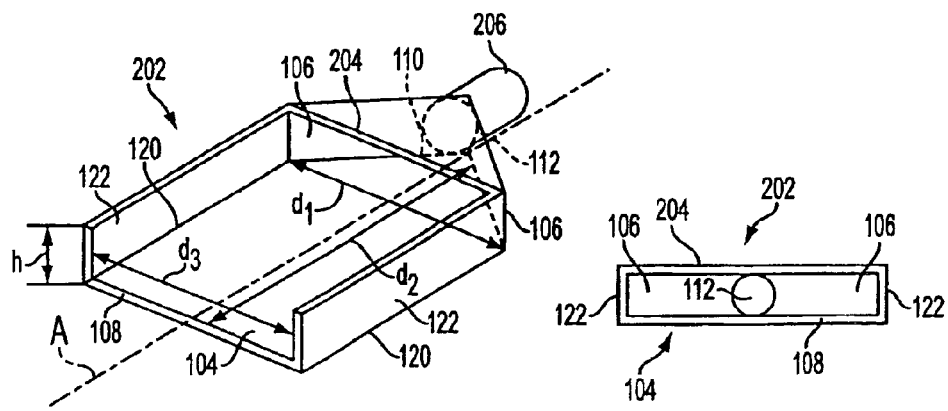
FIG. 7 is a perspective view of another needle-receiving port constructed in accordance with the present disclosure for use with an implantable patient access device.
Figure 8:
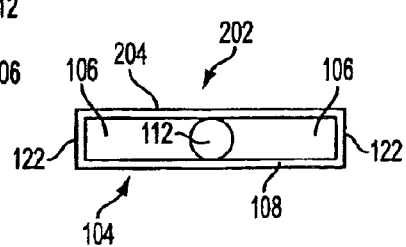
FIG. 8 is an elevational end view of the port of FIG. 7.
Figure 9:
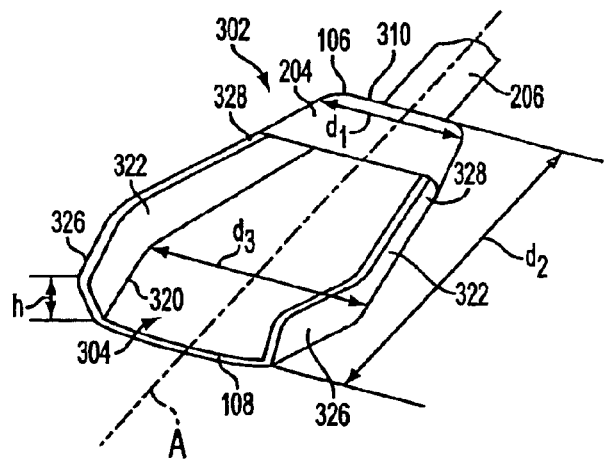
FIG. 9 is a perspective view of an additional needle-receiving port constructed in accordance with the present disclosure for use with an implantable patient access device.

Referring to FIGS. 7 and 8, another port 202 constructed in accordance with the present disclosure is shown. The port 202 of FIGS. 7 and 8 is similar to the port 102 of FIGS. 4 through 6 such that similar elements have the same reference characters. As shown, the port 202 further includes a cover 204 extending over the end walls 106, and a connection tube 206 extending from the end walls 106 and defining the entry region 112 of the port 202. In the embodiment of FIGS. 7 and 8, the side walls 122 are straight and extend parallel with the axis "A" such that "$d_3$" is substantially equal to "$d_1$".

FIGS. 9 through 13 show an additional port 302 constructed in accordance with the present disclosure. The port 302 of FIGS. 9 through 13 is similar to the port 202 of FIGS. 7 and 8 such that similar elements have the same reference characters. As shown, however, the port 302 includes a plate 304 having a second end 310 that is straight, instead of pointed, and extends substantially perpendicular with respect to the axis "A" of the port 302. Sides 320 of the plate 304 are pointed and extend outwardly from the axis "A", while side walls 322 of the port 302 follow the sides 320 of the plate 304 and have first portions 326 extending from the first end 108 of the plate to second portions 328 extending from the first portions 326 to the end walls 106. The first portions 326 of the side walls extend outwardly at an angle with respect to the axis "A" and the second portions 328 extend inwardly at an angle with respect to the axis "A", such that the greatest distance "$d_3$" between the side walls is at the junctures of the first and second portions.

Figure 10:
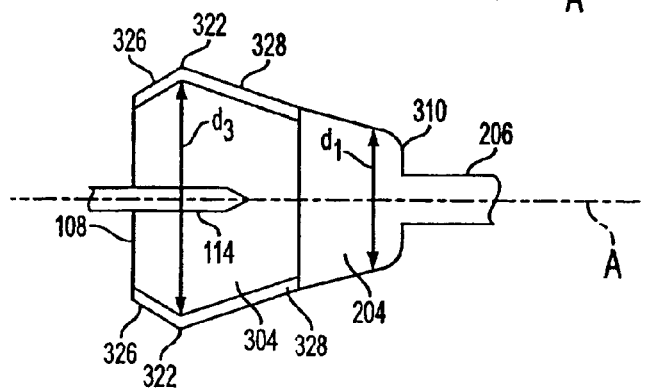
FIG. 10 is a top plan view of the port of FIG. 9 shown receiving a needle.
Figure 11:
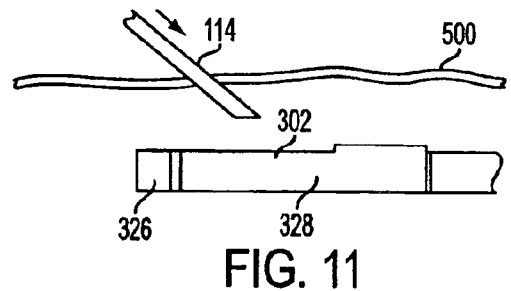
FIG. 11 is a side elevation view of the port of FIG. 9 shown implanted under skin and shown receiving a needle.
Figure 12:
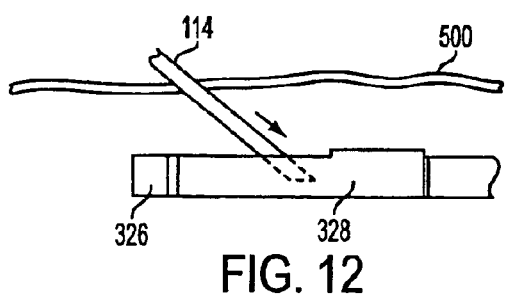
FIG. 12 is a side elevation view of the port of FIG. 9 shown implanted under skin and shown guiding the needle.
Figure 13:
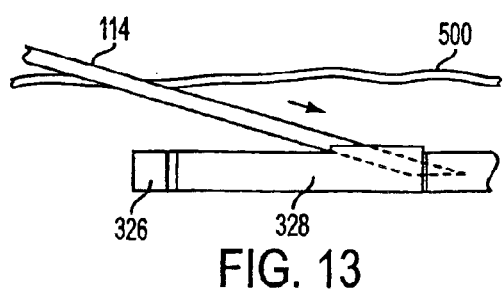
FIG. 13 is a side elevation view of the port of FIG. 9 shown implanted under skin and shown further guiding the needle.
Figure 14:
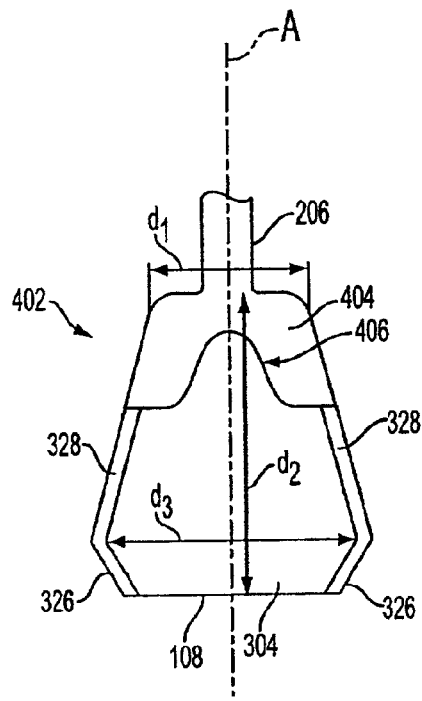
FIG. 14 is a top plan view of a further needle-receiving port constructed in accordance with the present disclosure for use with an implantable patient access device.
Figure 15:
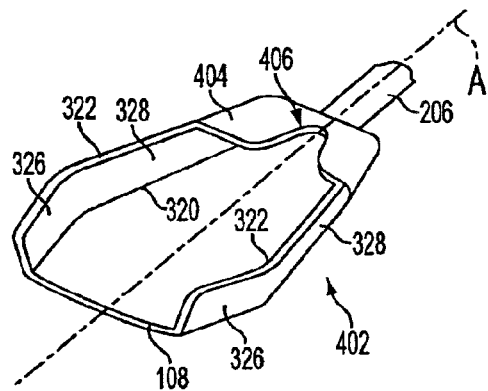
FIG. 15 is a perspective view of the port of FIG. 14.

As shown in FIG. 10, the plate 304 of the port 302 is for receiving a filament, such as a needle 114. FIGS. 11 through 13 show the port 302 implanted in a patient beneath an outer layer of skin, or epidermis 500. As shown in FIGS. 11 through 13, the side walls 322 and the end walls 106 of the port 302 help guide the needle 114 into the entry region 112 of the port 302.

Figure 16:
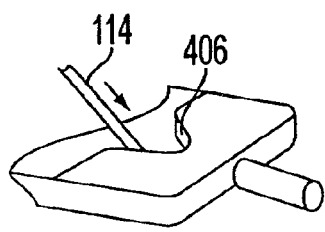
FIG. 16 is an opposite perspective view of a portion of the port of FIG. 14 shown receiving a needle.
Figure 17:
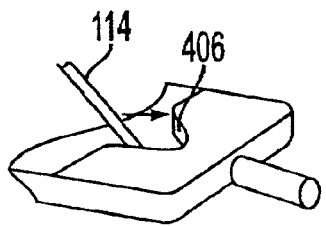
FIG. 17 is a perspective view of a portion of the port of FIG. 14 shown guiding the needle.
Figure 18:
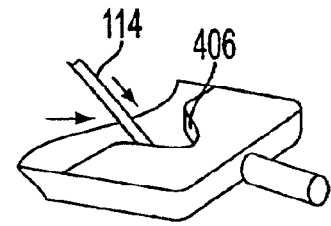
FIG. 18 is a perspective view of a portion of the port of FIG. 14 shown further guiding the needle.

A further port 402 constructed in accordance with the present disclosure is shown in FIGS. 14 through 18. The port 402 of FIGS. 14 through 18 is similar to the port 302 of FIGS. 9 through 13 such that similar elements have the same reference characters. As shown, however, the port 402 includes a cover 404 defining a slot 406, that extends parallel with the axis "A" of the port and is aligned with the entry region 112. As shown in FIGS. 16 through 18, the slot 406 further helps to guide a filament 114 into the entry region 112 of the port 402.

The specific ports described in this specification have been presented by way of illustration rather than limitation, and various modifications, combinations and substitutions may be effected by those skilled in the art without departure either in spirit or scope from this disclosure in its broader aspects and as set forth in the appended claims. All ports disclosed herein, and all elements thereof, are contained within the scope of at least one of the following claims. No elements of the presently disclosed ports are meant to be disclaimed.

We claim:

1. An implantable access device comprising a port for receiving and guiding a filament into an entry region of the implantable device, the port including:
   a plate for receiving a filament, the plate having opposing first and second ends; and
   at least two walls extending upwardly from the plate so that corners are formed between the plate and the walls, the walls each having opposing first and second edges, with the second edges defining an entry region for a filament at the second end of the plate, the first edges extending towards the first end of the plate, and a distance between the walls decreasing monotonically between the first and the second edges of the walls and from the first end to the second end of the plate.

2. A device according to claim 1, wherein a greatest distance between the walls is at least five times greater than a greatest height of the walls.

3. A device according to claim 2, wherein a greatest distance between the first and the second ends of the plate is at least five times greater than the greatest height of the walls.

4. An implantable access device comprising a port for receiving and guiding a filament into an entry region of the implantable device, the port including:
   a plate for receiving a filament, the plate having opposing first and second ends; and
   at least two walls extending upwardly from the plate, the wall each having opposing first and second edges, with the second edges defining an entry region for a filament at the second end of the plate, the first edges extending towards the first end of the plate, and a distance between the walls decreasing monotonically between the first and the second edges of the walls, wherein the second end of the plate is pointed and the entry region between the walls corresponds with a tip of the second end furthest from the first end of the plate.

5. A device according to claim 4, wherein the port includes a central longitudinal axis extending through the first and the second ends of the plate and the point of the second end of the plate is aligned with the axis.

6. A device according to claim 1, wherein the walls of the port extend perpendicular from the plate.

7. A device according to claim 1, wherein the plate of the port is substantially flat.

8. An implantable access device comprising a port for receiving and guiding a filament into an entry region of the implantable device, the port including:
   a plate for receiving a filament, the plate having opposing first and second end; and
   at least two walls extending upwardly from the plate, the walls each having opposing first and second edges, with the second edges defining an entry region for a filament at the second end of the plate, the first edges extending towards the first end of the plate, and a distance between the walls decreasing monotonically between the first and second edges of the walls, wherein the at least tow walls comprise end walls, the plate includes sides extending between the ends of the plate, and the port further includes opposing side walls extending from the sides of the plate and between the first end of the plate and the end walls.

9. A device according to claim 8, wherein a distance between the opposing side walls decreases monotonically between the first end of the plate and the end walls.

10. A device according to claim 1, wherein the port further includes at least one wing extending outwardly from the port and adapted to receive a fastener for fastening the port to tissue of a patient.

11. A device according to claim 1, further comprising a valve assembly disposed adjacent the entry region of the port, the valve assembly being normally closed and adapted to be opened by a filament guided through the entry region by the walls of the port.

12. A device according to claim 1, wherein the port is made from a material comprising at least one of titanium, stainless steel and ceramic.

13. An implantable access device comprising a port for receiving and guiding a filament into an entry region of the implantable device, the port including:
   an uncovered strike plate for receiving a filament, the plate having opposing first and second ends; and
   at least two walls extending upwardly from the plate so that corners are formed between the plate and the walls, the walls shaped and positioned to guide the filament moving between the first end and the second end of the plate towards an entry region defined between the walls and located substantially at the second end of the plate.

14. A device according to claim 13, wherein a greatest distance between the walls is at least five times greater than a greatest height of the walls.

15. A device according to claim 13, wherein a greatest distance between the first and the second ends of the plate is at least five times greater than a greatest height of the walls.

16. A device according to claim 13, wherein the plate of the port is substantially flat.

17. A device according to claim 13, wherein:
   the at least two walls comprise end walls;
   the plate includes sides extending between the ends of the plate; and
   the port further includes opposing side walls extending from the sides of the plate and between the first end of the plate and the end walls, and wherein the side walls are shaped and positioned to guide the filament moving between the first end and the second end of the plate towards the end walls.

18. A device according to claim 13, wherein the port further includes at least one wing extending outwardly from the port and adapted to receive a fastener for fastening the port to tissue of a patient.

19. A device according to claim 13, further comprising a valve assembly disposed adjacent the entry region of the port, the valve assembly being normally closed and adapted to be opened by a filament guided through the entry region by the walls of the port.

20. A device according to claim 13, wherein the port is made from a material comprising at least one of titanium, stainless steel and a ceramic.

21. An implantable access device comprising:
   a port for receiving a filament and guiding the filament through an entry region of the port, wherein the port includes an uncovered, substantially flat strike plate and each of a greatest width and a greatest length of the uncovered strike plate of the port is at least five times greater than a height of the port; and
   a valve assembly disposed adjacent the entry region of the port, the valve assembly being normally closed and adapted to be opened by a filament guided along the uncovered strike plate and through the entry region of the port.

22. An implantable access device according to claim 21, further comprising walls extending upwardly from the strike plate such that corners are formed between the walls and the strike plate the port.

23. A device according to claim 8, wherein the side walls of the port extend perpendicular from the plate.

24. A device according to claim 8, wherein the port includes a central axis extending through the first and the second ends of the plate and the side walls include first portions extending from the first end of the plate to second portions extending from the first portions to the end walls, and wherein the first portions extend outwardly at an angle with respect to the axis and the second portions extend inwardly at an angle with respect to the axis.

25. A device according to claim 1, wherein the port further includes a cover extending over the walls.

26. A device according to claim 25, wherein the cover includes a slot aligned with the entry region between the walls.

27. A device according to claim 13, wherein the walls of the port extend perpendicular from the plate.

28. A device according to claim 17, wherein the side walls of the port extend perpendicular from the plate.

29. A device according to claim 13, wherein the port further includes a cover extending over the walls.

30. A device according to claim 29, wherein the cover includes a slot aligned with the entry region between the walls.

* * * * *